United States Patent [19]

Bernstein et al.

[11] Patent Number: 5,656,297
[45] Date of Patent: *Aug. 12, 1997

[54] MODULATED RELEASE FROM BIOCOMPATIBLE POLYMERS

[75] Inventors: Howard Bernstein; Yan Zhang, both of Cambridge, Mass.; M. Amin Khan, Downingtown, Pa.; Mark A. Tracy, Arlington, Mass.

[73] Assignee: Alkermes Controlled Therapeutics, Incorporated, Cambridge, Mass.

[*] Notice: The portion of the term of this patent subsequent to Jul. 25, 2014, has been disclaimed.

[21] Appl. No.: 237,057

[22] Filed: May 3, 1994

Related U.S. Application Data

[63] Continuation-in-part of Ser. No. 849,754, Mar. 12, 1992, abandoned.

[51] Int. Cl.[6] .............................. A61K 9/14; A61K 9/16
[52] U.S. Cl. ......................... 424/484; 424/486; 424/487; 424/488; 424/489; 514/772.3; 514/772.6; 514/781; 514/805; 514/965
[58] Field of Search ........................ 424/489, 426, 424/425, 428, 486, 484, 487, 488; 514/772.3, 772.6, 781, 965

[56] References Cited

U.S. PATENT DOCUMENTS

| | | | |
|---|---|---|---|
| 3,523,906 | 8/1970 | Vrancken et al. | 252/316 |
| 3,691,090 | 9/1972 | Kitajima et al. | 252/316 |
| 3,737,337 | 6/1973 | Schnoriag et al. | 117/100 |
| 3,887,699 | 6/1975 | Yolles | 424/19 |
| 4,237,114 | 12/1980 | Cardarelli | 424/78 |
| 4,389,330 | 6/1983 | Tice et al. | 427/213.36 |
| 4,530,840 | 7/1985 | Tice et al. | 514/179 |
| 4,542,025 | 9/1985 | Tice et al. | 424/78 |
| 4,655,777 | 4/1987 | Dunn et al. | 623/16 |
| 4,675,189 | 6/1987 | Kent et al. | 424/490 |
| 4,767,628 | 8/1988 | Hutchinson | 424/426 |

(List continued on next page.)

FOREIGN PATENT DOCUMENTS

| | | |
|---|---|---|
| 0 580 428A1 | 1/1994 | European Pat. Off. |
| 0 633 020A1 | 1/1995 | European Pat. Off. |
| WO91/12882 | 2/1991 | WIPO |
| WO93/17668 | 9/1993 | WIPO |
| WO94/07469 | 4/1994 | WIPO |
| WO94/12158 | 6/1994 | WIPO |

OTHER PUBLICATIONS

Pratt, Lawrence et al., "The Effect of Ionic Electrolytes on Hydrolytic Degradation of Biodegradable Polymers: Mechanical and Thermodynamic Properties and Molecular Modeling," *J. Polymer Science* 31 (7):1759–1769 Jan. 1993.

*Primary Examiner*—Thurman K. Page
*Assistant Examiner*—James M. Spear
*Attorney, Agent, or Firm*—Hamilton, Brook, Smith & Reynolds, P.C.

[57] ABSTRACT

The present invention relates to a composition for the modulated release of a biologically active agent. The composition comprises a biocompatible polymeric matrix, a biologically active agent which is dispersed within the polymeric matrix, and a metal cation component which is separately dispersed within the polymeric matrix, whereby the metal cation component modulates the release of the biologically active agent from the polymeric matrix. The present invention also relates to a method for modulating the release of a biologically active agent from a biocompatible polymeric matrix, comprising the steps of dissolving a biocompatible polymer in a solvent to form a polymer solution and also separately dispersing a metal cation component and a biologically active agent within the polymer solution. The polymer solution is then solidified to form a polymeric matrix, wherein at least a significant portion of the metal cation component is dispersed in the polymeric matrix separately from the biologically active protein, and whereby the metal cation component modulates the release of the biologically active agent from the polymeric matrix.

23 Claims, 9 Drawing Sheets

U.S. PATENT DOCUMENTS

| | | | |
|---|---|---|---|
| 4,835,139 | 5/1989 | Tice et al. | 514/15 |
| 4,891,225 | 1/1990 | Langer et al. | 424/428 |
| 4,906,474 | 3/1990 | Langer et al. | 424/428 |
| 4,962,091 | 10/1990 | Eppstein et al. | 514/2 |
| 4,981,696 | 1/1991 | Loomis et al. | 424/486 |
| 5,019,400 | 5/1991 | Gombotz et al. | 424/497 |
| 5,075,115 | 12/1991 | Brine | 424/486 |
| 5,145,674 | 9/1992 | Lane et al. | 424/78.08 |
| 5,344,654 | 9/1994 | Rueger et al. | 424/423 |

MODULATED RELEASE FROM BIOCOMPATIBLE POLYMERS

RELATED APPLICATIONS

This is a continuation-in-part of U.S. patent application Ser. No. 07/849,754, filed Mar. 12, 1992, now abandoned the teachings of which are hereby incorporated by reference.

BACKGROUND

Many illnesses or conditions require a constant level of medicaments or agents in vivo to provide the most effective prophylactic, therapeutic or diagnostic results. In the past, medicaments were given in doses at intervals which resulted in fluctuating medication levels.

Attempts to control and steady medication levels have more recently included the use of many biodegradable substances, such as poly(lactide) or poly(lactide-co-glycolide) microspheres containing the medicament. The use of these microspheres provided an improvement in the controlled release of medicaments by utilizing the inherent biodegradability of the polymer to improve the release of the medicament and provide a more even, controlled level of medication. However, in some cases, biodegradable polymers under in vivo conditions can have an initial level of medicament release, which is too high or too low, and after a period of hydration can substantially degrade to thereby limit the effective life of the controlled release microspheres. Therefore, a need exists for a means of modulating the controlled release of medicament from a biodegradable polymer to provide a higher level of initial medicament release and to provide longer periods of fairly consistent medicament release levels in vivo.

SUMMARY OF THE INVENTION

The present invention relates to a composition for the modulated release of a biologically active agent. The composition comprises a biocompatible polymeric matrix, a biologically active agent which is dispersed within the polymeric matrix, and a metal cation component which is separately dispersed within the polymeric matrix, whereby the metal cation component modulates the release of the biologically active agent from the polymeric matrix.

The present invention also relates to a method for modulating the release of a biologically active agent from a polymeric matrix, comprising the steps of dissolving a. biocompatible polymer in a solvent to form a polymer solution and also separately dispersing a metal cation component and a biologically active agent within said polymer solution. The polymer solution is then solidified to form a polymeric matrix, wherein at least a significant portion of the metal cation component is dispersed in the polymeric matrix separately from the biologically active protein, and whereby the metal cation component modulates the release of the biologically active agent from the polymeric matrix.

This invention has the advantage of modulating the release of a biologically active agent in vivo from a biodegradable polymer, thereby enhancing the control of the level of prophylactic, therapeutic and diagnostic agents released in vivo and lengthening the period during which controlled release can be maintained for a single dose.

DETAILED DESCRIPTION OF THE INVENTION

Figure 1:
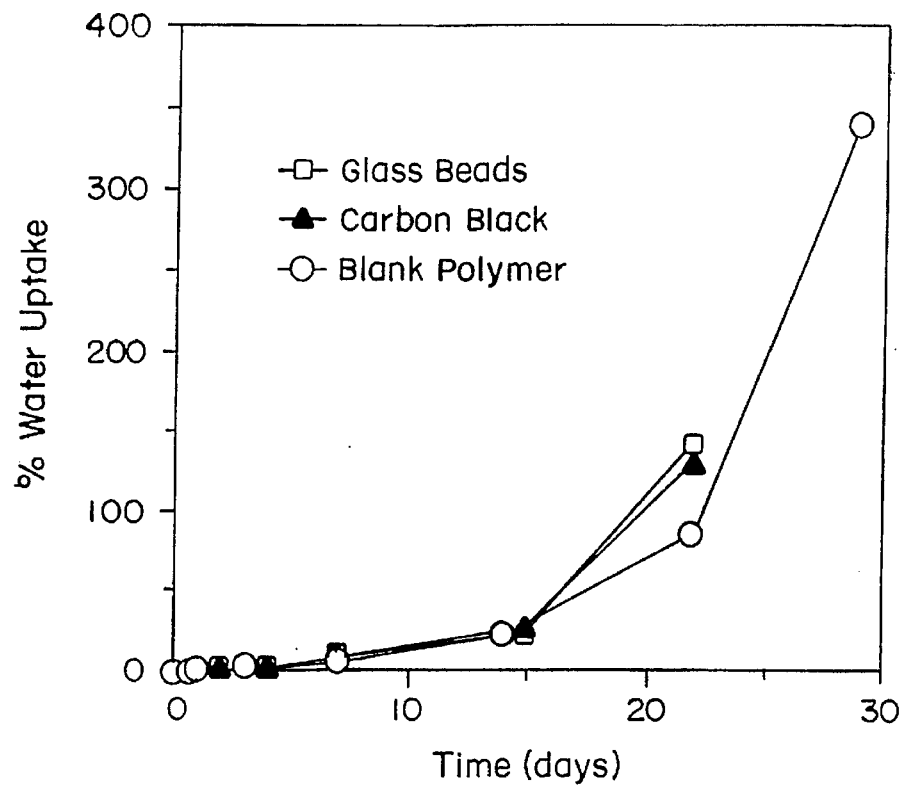
FIG. 1 is a plot of percent water uptake (%w/w) as a function of time in 10 mM HEPES for the following polymer films: a) blank PLGA, b) PLGA containing glass beads, and c) PLGA containing carbon black, illustrating the effect of glass beads and carbon black on PLGA film water absorption.

A modulated release of a biologically active agent, as defined herein, is a release of a biologically active agent from a biocompatible polymeric matrix containing a dispersed metal cation component which is separate from the biologically active agent. In a modulated release, at least one release characteristic, such as initial release level of said agent, subsequent agent release levels, the amount of agent released and/or the extent of the release period, are changed from the release characteristic(s) demonstrated for said biologically active agent from a polymeric matrix not containing a dispersed metal cation component.

A polymer of the polymeric matrix of this composition is a biocompatible polymer which can be either a biodegradable or non-biodegradable polymer, or blends or copolymers thereof.

Biodegradable, as defined herein, means the composition will degrade or erode in vivo to form smaller chemical species. Degradation can result, for example, by enzymatic, chemical and physical processes. Suitable biocompatible, biodegradable polymers include, for example, poly(lactide)s, poly(glycolide)s, poly(lactide-co-glycolide)s, polyanhydrides, polyorthoesters, polyetheresters, polycaprolactone, polyesteramides, blends and copolymers thereof.

Biocompatible, non-biodegradable polymers suitable for the modulated release composition of this invention include non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

A polymer, or polymeric matrix, is biocompatible if the polymer, and any degradation products of the polymer, are non-toxic to the recipient and also present no significant deleterious or untoward effects on the recipient's body.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 5,000 Daltons to about 42,000 Daltons A biologically active agent, as defined herein, is an agent which possesses therapeutic, prophylactic or diagnostic properties in vivo. Examples of suitable therapeutic and/or prophylactic biologically active agents include proteins, such as hormones, antigens, growth factors, etc.; nucleic acids, such as antisense molecules; and small molecules, such as antibiotics, steroids, decongestants, neuroactive agents, anesthetics and sedatives. Examples of suitable diagnostic and/or therapeutic biologically active agents include radioactive isotopes and radiopaque agents.

In the modulated release composition of the present invention, an effective amount of particles of a biologically active agent is dispersed within a polymeric matrix. An effective amount of a biologically active agent is a therapeutically, prophylactically or diagnostically effective amount, which can be determined by a person of ordinary skill in the art taking into consideration factors such as body weight; age; physical condition; therapeutic, prophylactic or diagnostic goal desired, type of agent used, type of polymer used, initial burst and subsequent release levels desired, and release rate desired. Typically, a polymeric matrix for modulating the release of a biologically active agent will contain from about 0.01% (w/w) biologically active agent to about 50% (w/w) biologically active agent, by weight.

In one embodiment, a biologically active agent is a protein. Preferred proteins for inclusion in a modulated release composition include, for example, nucleases, erythropoietin, human growth hormone, interferons, interleukins, tumor necrosis factor, adrenocorticotropic hormone, growth factors, and colony-stimulating factors.

A modulated controlled release composition may also contain more than one biologically active agent, for instance, two different proteins, such as erythropoietin and granulocyte-macrophage colony-stimulating factor.

A metal cation component, as defined herein, is a component containing at least one kind of multivalent metal cation in a non-dissociated state, a dissociated state, or a combination of non-dissociated and dissociated states. Suitable metal cation components include, for instance, metal salts, metal hydroxides, and basic (pH of about 7 or higher) salts of weak acids wherein the salt contains a metal cation. It is preferred that the metal cation be divalent.

In the modulated release composition of the present invention, a suitable concentration of a metal cation component is dispersed within a polymer matrix. A suitable concentration of a metal cation component is any concentration of a metal cation component which will modulate the release of a biologically active agent from a polymeric matrix. In one embodiment, suitable proportions of a metal cation component to be dispersed in a polymer is between about 2% (w/w) to about 30% (w/w). The optimum ratio depends upon the polymer, the metal cation component and the biologically active agent utilized. In a preferred embodiment, suitable amounts of a metal cation component to be dispersed in a polymer is between about 5% (w/w) to about 20% (w/w).

In one embodiment, the metal cation component is substantially insoluble in aqueous fluids. Substantial insolubility in aqueous fluids, as defined herein means that the metal cation component is generally not soluble, or is of low solubility, in water or fluids, such as PBS, HEPES or alimentary track fluids. Examples of suitable insoluble metal cation components include, or contain, for instance, $Mg(OH)_2$, $MgCO_3$ (such as $4MgCO_3 \cdot Mg(OH)_2 \cdot 5H_2O$), $ZnCO_3$ (such as $3Zn(OH)_2 \cdot 2ZnCO_3$), $CaCO_3$ and $Zn_3(C_6H_5O_7)_2$ (hereinafter zinc citrate).

In an alternate embodiment, the metal cation component is substantially soluble in aqueous fluids. Substantial solubility in aqueous fluids, as defined herein means that the metal cation component is generally soluble in water or fluids, such as PBS, HEPES or alimentary track fluids. Suitable soluble metal cation components include, or can contain, for example, $Mg(OAc)_2$, $MgSO_4$, $Zn(OAc)_2$, $ZnSO_4$, $ZnCl_2$, $MgCl_2$ and $Mg_3(C_6H_5O_7)_2$ (hereinafter magnesium citrate).

In one embodiment of the method for modulating the release of a biologically active agent from a polymeric matrix, a suitable polymer is dissolved in a solvent to form a polymer solution. Examples of suitable solvents include, for instance, polar organic solvents such as methylene chloride, chloroform, tetrahydrofuran, dimethyl sulfoxide and hexafluoro-isopropanol.

Particles of at least one metal cation component are then dispersed within the polymer solution. Suitable means of dispersing a metal cation component within a polymer solution include sonication, agitation, mixing and homogenization. It is understood that a metal cation component can be added directly to the polymer solution as a solid, preferentially in particulate form, wherein the metal cation component will either then be suspended as solid particles dispersed within the polymer solution or the metal cation component will then dissociate within the polymer solution to form free metal cations. It is also understood that, before addition to a polymer solution, a metal cation component can be suspended as solid particles or dissolved in a second solvent, wherein the second solvent is then added to the polymer solution. A second solvent is suitable if it is the same solvent as the polymer's solvent, or if the second solvent is miscible with the polymer's solvent and the polymer is soluble in the second solvent. An example of a suitable second solvent is acetone.

In another embodiment, a metal cation component can be suspended or dissolved in a solvent, after which, a suitable polymer is then dissolved in said solvent.

At least one biologically active agent is also added to the polymer solution separately from the addition of the metal cation component, metal cation component suspension, or metal cation component solution. In one embodiment, the biologically active agent is dissolved in a solvent, which is also suitable for the polymer, and then mixed into the polymer solution.

It is to be understood that a metal cation component and a biologically active agent can be added to the polymer solution sequentially, in reverse order, intermittently or through separate, concurrent additions. It is also understood that a biologically active agent can be suspended in a solution, or suspension, of a metal cation component in a solvent before dissolving the polymer in said solvent.

The amount of a biologically active agent added to the polymer solution can be determined empirically by comparative in vitro tests of polymeric matrices containing different concentrations of at least one metal cation component and of at least one biologically active agent. The amount used will vary depending upon the particular agent, the desired effect of the agent at the planned release levels, and the time span over which the agent will be released.

In an alternate embodiment, the protein added to the polymer solution can be mixed with an excipient, such as at least one stabilizing agent as is known in the art.

The formation of a polymeric matrix microparticle for modulating the release of RNase-A is further described in Example VII. The effectiveness of the method of modulating the release of RNase-A from a polymeric matrix is also described in Example VII.

The polymeric matrix of this invention can be formed into many shapes such as a film, a pellet, a cylinder, a disc or a microparticle. A microparticle, as defined herein, comprises a particle having a diameter of less than about one millimeter containing particles of a biologically active agent dispersed therein. A microparticle can have a spherical, non-spherical or irregular shape. The preferred microparticle shape is a sphere.

In a preferred embodiment, the method includes forming a modulated release polymeric matrix as a microparticle. A suitable metal cation component is dispersed as solid particles or free dissociated cations, and a biologically active agent is separately dispersed as solid particles in a polymer solution containing about 5–30% polymer by weight. In a more preferred embodiment, the polymer solution contains about 5–15% polymer by weight. Biodegradable polymers are preferred, while PLGA is more preferred.

A microparticle is then formed from the polymer solution. A suitable method for forming an acceptable microsphere from a polymer solution is described in U.S. Pat. No. 5,019,400, issued to Gombotz et al. The teachings of U.S. Pat. No. 5,019,400 are incorporated herein by reference.

In another embodiment, a modulated release composition is prepared by the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al., which are incorporated herein by reference.

In the solvent evaporation method a polymer solution, which contains a dispersed metal cation component and a dispersed biologically active agent, is mixed in or agitated with a continuous phase, in which the polymer's solvent is substantially immiscible, to form an emulsion. The continuous phase is usually an aqueous solvent. Emulsifiers are often included in the continuous phase to stabilize the emulsion. The polymer's solvent is then evaporated over a period of several hours or more, thereby solidifying the polymer to form a polymeric matrix having a metal cation component and a biologically active agent separately dispersed therein.

In another embodiment, the method includes forming a modulated release polymeric matrix as a film or any other shape. A polymer solution and metal cation component, in particulate or dissociated form, is mixed, for instance by sonication, until the metal cations are generally dispersed throughout the polymer solution. The polymer solution is subsequently cast in a mold, such as a petri dish. The solvent is then removed by means known in the art until a film or form, with a constant dry weight, is obtained. The formation of polymeric matrix films is further described in Example I.

Several other methods of using the composition of this invention can be used to modulate physical properties of polymers. One embodiment of the method of use consists of a method for modifying the water absorption, or hydration capacity without significant polymer degradation. The method comprises forming a solution of a polymer and then dispersing a metal cation component into the polymer solution. The polymer solution is then solidified to form a polymer matrix wherein the metal cation component is dispersed therein. See Example II for a further description of this method of enhancing initial hydration.

A further embodiment of the method of use consists of a method for significantly stabilizing the glass transition temperature for a polymer during hydration, comprising the steps of forming a solution of a polymer and a solvent and then dispersing a metal cation component within said polymer solution. The polymer solution is then solidified to form a polymer matrix wherein particles of the metal cation component are dispersed therein.

Glass transition temperature (Tg) could be an indirect indicator of polymeric degradation since Tg is a function of the molecular weight of the polymer and usually decreases as molecular weight decreases. Glass transition temperature (Tg) is defined as the temperature at which a polymer converts from a glass phase to a rubbery phase. Tg is affected by the molecular weight of the polymer. See Example IV for further description of this method of stabilizing Tg during polymer hydration. In the embodiment wherein the polymeric matrix is in the form of microparticles, the stabilization of Tg maintains the mechanical properties of the polymer, thereby enhancing the control of agent release.

Yet another embodiment of the method of use consists of a method for increasing the porosity of a polymer without significant polymer degradation. This method includes the steps of forming a solution of a polymer and a solvent and then dispersing a metal cation component into said polymer solution. The polymer solution is then solidified to form a polymer matrix wherein the metal cation compound is dispersed therein and subsequently hydrated to form at least one gap within said polymeric matrix, thereby increasing the porosity of the polymer. Gaps, as defined herein comprise pores and/or voids. See Example V for a further description of this method of use.

An alternate embodiment of the method of use consists of a method for slowing the rate of degradation of a polymer. In this method a solution is formed of a polymer and a metal cation component is then dispersed within said polymer solution. The polymer solution is subsequently solidified to form a polymeric matrix having a metal cation component dispersed therein. Example III provides additional description of the slowing of the polymeric degradation rate.

The composition of this invention can be administered to a human, or other animal, by injection and/or implantation subcutaneously, intramuscularly, intraperitoneally, intradermally, intravenously, intraarterially or intrathecally; by administration to mucosal membranes, such as intranasally or by means of a suppository, or by in situ delivery to provide the desired dosage of a biologically active agent based on the known parameters for treatment of the various medical conditions with said agent.

The invention will now be further and specifically described by the following examples.

EXEMPLIFICATION

EXAMPLE I

Preparation of Polymer Films Containing Salts

PLGA (50:50) with a molecular weight of 42,000 Daltons (I.V. 0.7 dL/g Birmingham Polymers, Birmingham Ala.) was used for all film studies. The polymer films were produced by a film casting technique. The polymer was dissolved in methylene chloride (5% w/v) at room temperature for up to 24 hours.

Films were prepared using both water insoluble and soluble salts containing divalent cations. The salts were incorporated either as particulates or by cosolubilizing the salts with the polymer in an appropriate cosolvent. The fabrication procedure is described below.

Three salts with low water solubility, $MgCO_3$, $Mg(OH)_2$ and $ZnCO_3$ (Spectrum Chemical MFG, Corp., Gardena, Calif.) and two water soluble salts, $MgSO_4$ and $ZnSO_4$ (Spectrum Chemical MFG, Corp., Gardena, Calif.) were incorporated into films as particulates. $MgCOs$, $Mg(OH)_2$ and $ZnCO_3$ were sieved prior to film casting using a 38 micron U.S.A. standard testing sieve to control the particle size. The average particle diameter of the sieved salts prior to encapsulation is provided in Table 1.

TABLE 1

| Salt | Formula | Diameter (μm) |
|---|---|---|
| $MgCO_3$ | $4MgCO_3 \cdot Mg(OH)_2 \cdot 5H_2O$ | 2.5 |
| $Mg(OH)_2$ | $Mg(OH)_2$ | 2.5 |
| $ZnCO_3$ | $3Zn(OH)_2 \cdot 2ZnCO_3$ | 4.0 |

As non-ionic water insoluble particulates, either carbon black or glass particles (20 micron diameter, Polysciences Inc. Warrington, Pa.) were used. Polymer films were prepared by adding the sieved salt to the polymer solution to a final concentration in the 0–30% (w/w, salt/polymer) range. The salt polymer suspension was sonicated for approximately four minutes to disperse the salt particles. A sample of 100 mL of the suspension was then cast in 9×5×1 inch teflon petri dish (Plastic Structures Co., Wilmington, Mass.). The films were cast in two layers to avoid settling of the salt particles. The methylene chloride was evaporated at room temperature in a hood for the first 24 hours at atmospheric pressure. The films were transferred to a vacuum oven and were dried at 30° C. for 6 hours, 40° C. for 3 days, and then at 50° C. for 3 days. No further reduction in dry weight was observed at the end of this drying cycle.

Polymer films containing the water soluble salts magnesium acetate and zinc acetate were prepared by cosolubilizing the salts with PLGA in acetone. A 10% solution of polymer was prepared by dissolving 5 g of polymer in 50 mL of acetone at room temperature. A solution of $Mg(OAc)_2$ or $Zn(OAc)_2$ was prepared by dissolving 0.26 g of either salt in 50 mL of room temperature acetone. Equal volumes of the salt solution and the polymer solution were combined and the mixture was sonicated for approximately four minutes. One hundred milliliter samples of the salt-polymer solution were poured into the teflon petri dishes. The methylene chloride was evaporated as described previously.

EXAMPLE II

Water Uptake in Polymeric Films

Water uptake studies were conducted on the polymeric films made in Example I. The buffer solutions used in this study were HEPES (10 mM HEPES, 130 mM NaCl, 0.1% $NaN_3$, 1% Pluronics F68, pH 7.3) or PBS (50 mM Sodium Phosphate, 78 mM NaCl, 0.1% $NAN_3$, 1% Pluronics F68, pH 7.2). Film samples (50–80) mg were incubated in buffer (.5 ml/mg film) at 37° C. Duplicate film samples were utilized for each of the time points to enable both dry and wet weight measurements.

Samples were recovered at the specified time intervals, the surface water removed with absorbent paper and the samples were weighed. The samples were then frozen at −80° C. and subsequently lyophilized for 3–4 days until constant dry weight. The weights of the dried films were measured after lyophilization. Buffer solution was replaced in full for the film samples being incubated for the later water uptake determinations.

Water uptake was calculated at each time point using the following equation:

$$\% H_2O\ Uptake = \frac{Wt.\ hydrated\ film - Wt.\ dried\ film}{Wt.\ dried\ film} \times 100$$

Values obtained for duplicate samples were averaged.

The effects of different salts on the water uptake of the PLGA films are shown in FIGS. 1–8. The control films (blank films) without incorporated salts showed a slow, gradual increase in the amount of water absorbed during the first 15 to 20 days (FIG. 1). After this time, a large increase in water uptake was observed. This secondary phase of water uptake was associated with polymer degradation (see Example III). Films containing inert particles (carbon black or glass particles) exhibited water uptake profiles similar to the control polymer films (FIG. 1).

Figure 2:
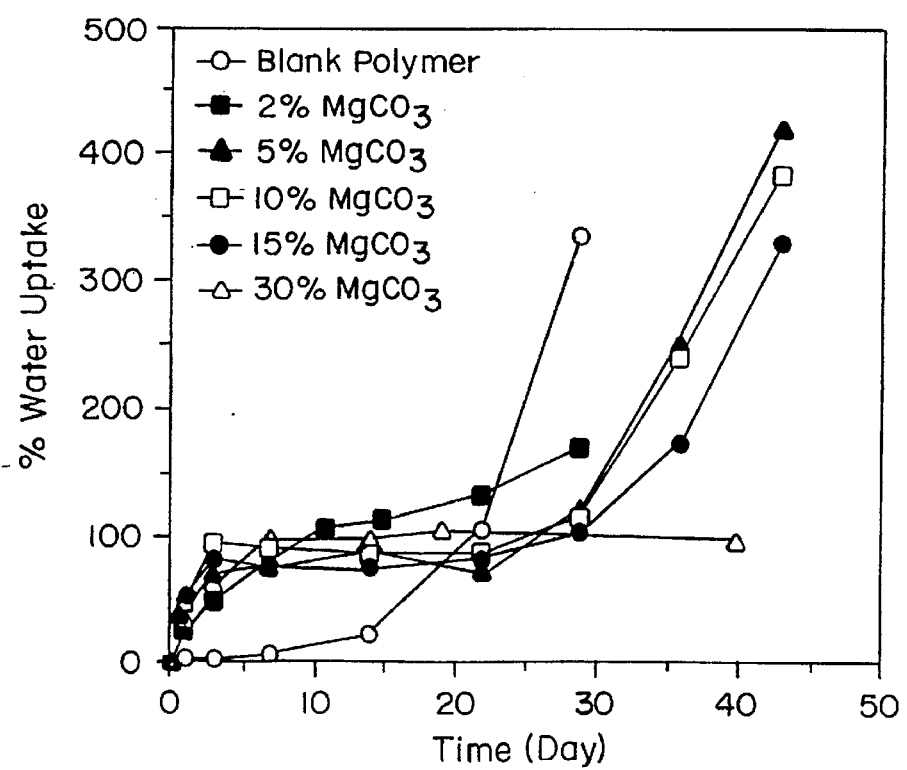
FIG. 2 is a plot of percent water uptake (%w/w) as a function of hydration time in 10 mM HEPES for the following polymer films: a) blank PLGA, b) PLGA containing 2% $MgCO_3$, c) PLGA containing 5% $MgCO_3$, d) PLGA containing 10% $MgCO_3$, e) PLGA containing 15% $MgCO_3$, and f) PLGA containing 30% $MgCO_3$, illustrating the effect of $MgCO_3$ at different concentrations on PLGA film water absorption.
Figure 3:
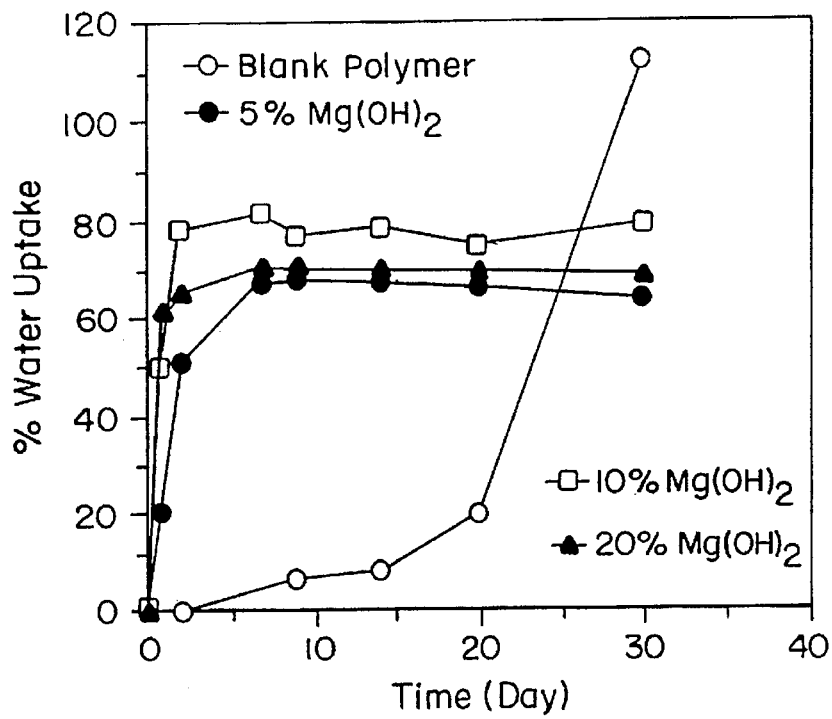
FIG. 3 is a plot of percent water uptake (%w/w) as a function of hydration time in 50 mM PBS for the following polymer films: a) blank PLGA, b) PLGA containing 5% $Mg(OH)_2$, c) PLGA containing 10% $Mg(OH)_2$, and d) PLGA containing 20% $Mg(OH)_2$, illustrating the effect of at different concentrations on PLGA film water absorption.
Figure 4:
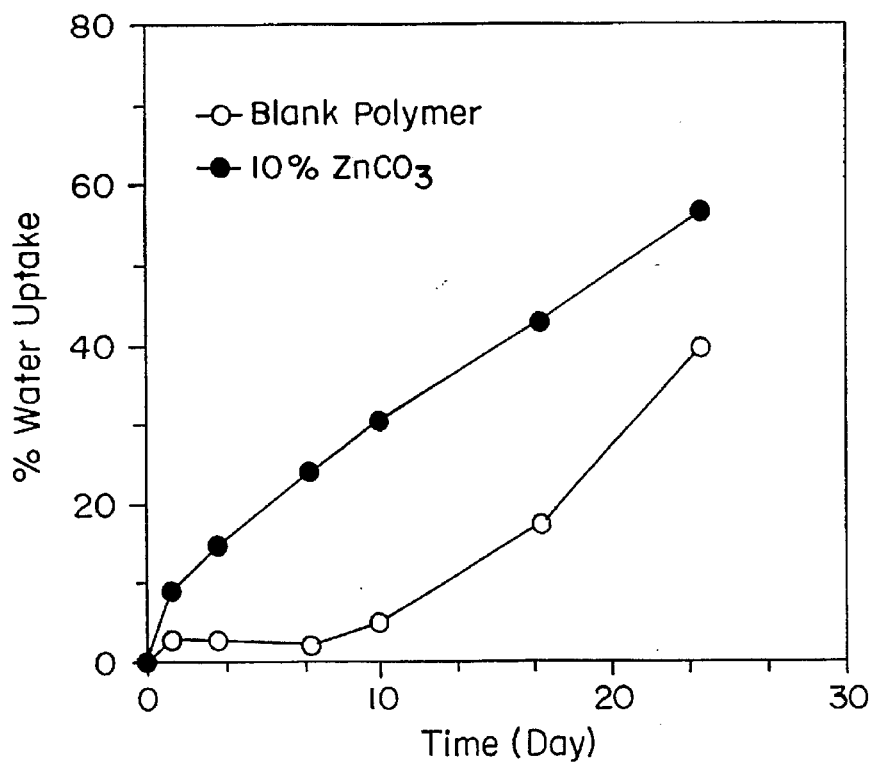
FIG. 4 is a plot of percent water uptake (%w/w) versus hydration time in 50 mM PBS for the following polymer films: a) blank PLGA and b) PLGA, containing 10% $ZnCO_3$, illustrating the effect of $ZnCO_3$ on PLGA film water absorption.
Figure 5:
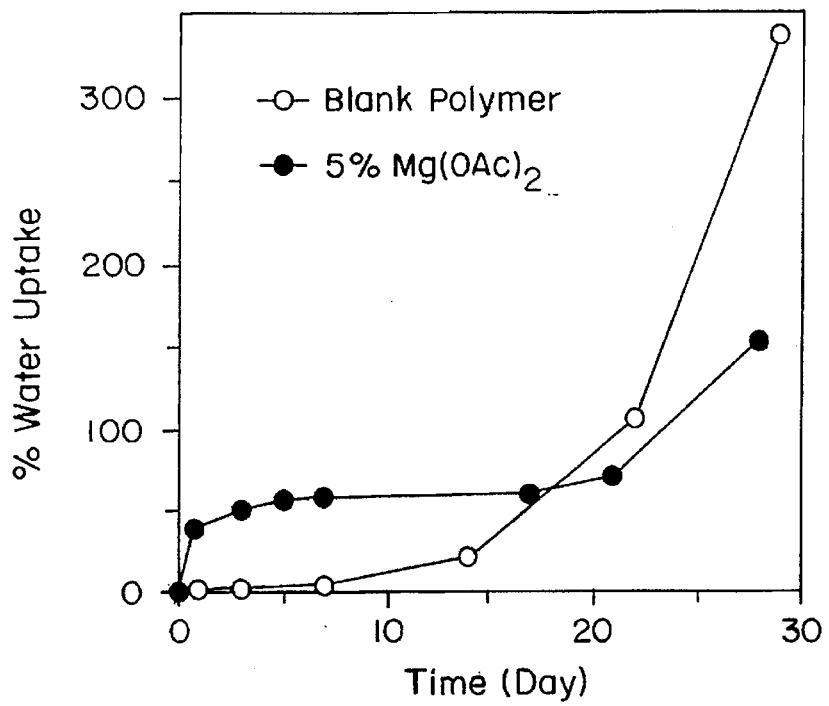
FIG. 5 is a plot of percent water uptake (%w/w) versus hydration time in 10 mM HEPES for the following polymer films: a) blank PLGA and b) PLGA, containing 5% $Mg(OAc)_2$, illustrating the effect of $Mg(OAc)_2$ on PLGA film water absorption.

Films containing insoluble salts ($MgCO_3$, $Mg(OH)_2$ and $ZnCO_3$) all exhibited a greater initial water uptake than control films (FIGS. 2–4). Following the initial uptake phase, about 3 days, the amount of water absorbed by the films containing $MgCO_3$ and $Mg(OH)_2$ did not change until after 30 days. The second phase of water uptake occurred, approximately 2 weeks later than was observed with control polymer films.

$ZnCO_3$ films exhibited a more continuous water uptake of a magnitude greater than that of control films (FIG. 4). There was no clear distinction between initial and secondary water uptake phases in the $ZnCO_3$ films.

Figure 6:
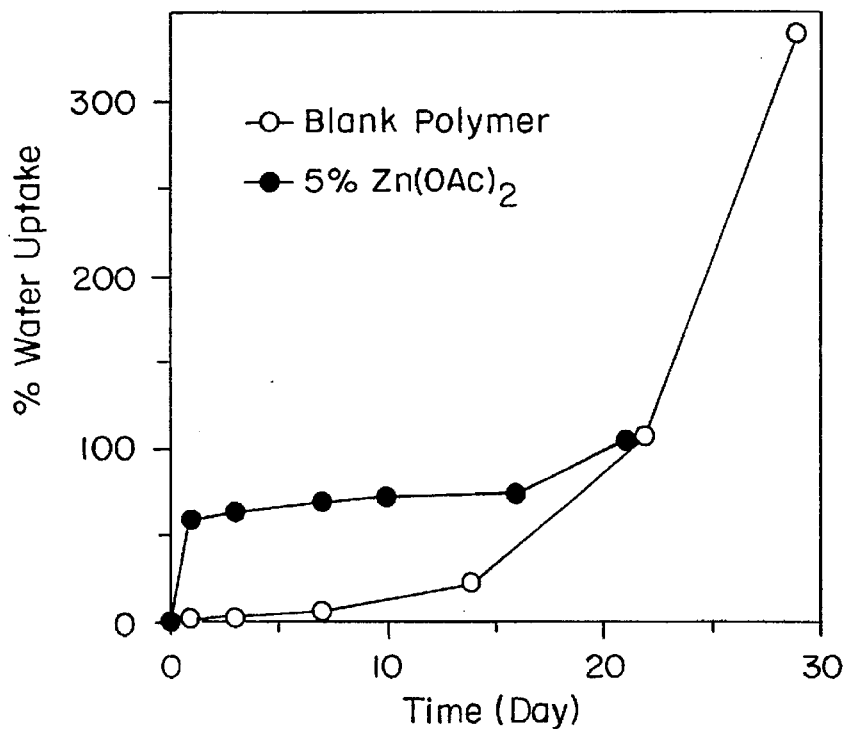
FIG. 6 is a plot of percent water uptake (%w/w) versus hydration time in 10 mM HEPES for the following polymer films: a) blank PLGA and b) PLGA, containing 5% $Zn(OAc)_2$, illustrating the effect of $Zn(OAc)_2$ on PLGA film water absorption.
Figure 7:
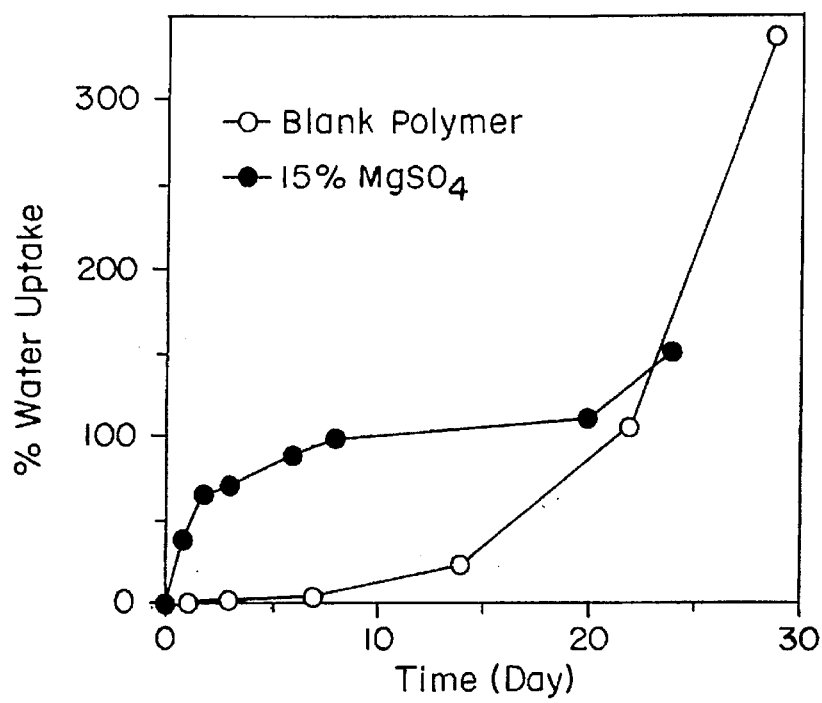
FIG. 7 is a plot of percent water uptake (%w/w) versus hydration time in 10 mM HEPES for the following polymer films: a) blank PLGA and b) PLGA, containing 15% $MgSO_4$, illustrating the effect of $MgSO_4$ on PLGA film water absorption.
Figure 8:
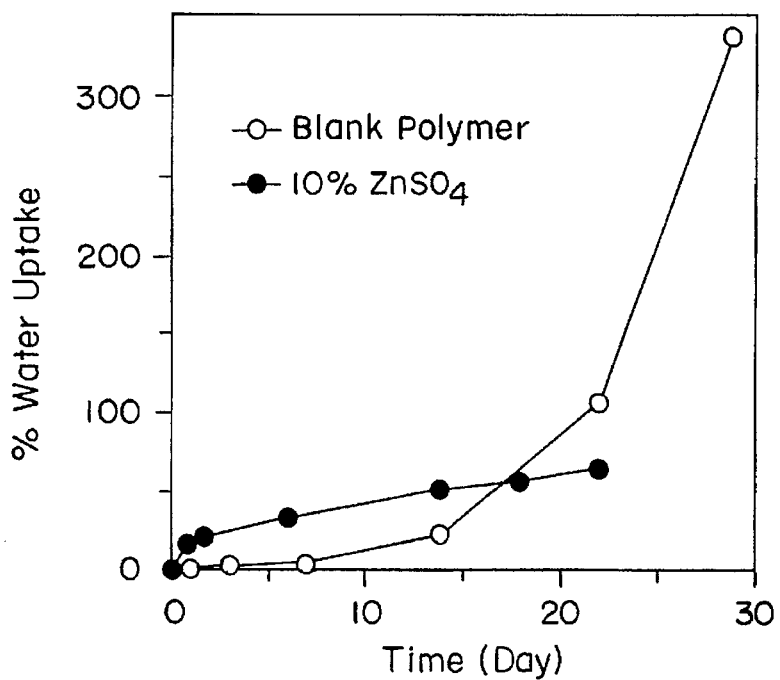
FIG. 8 is a plot of percent water uptake (%w/w) versus hydration time in 10 mM HEPES for the following polymer films: a) blank PLGA and b) PLGA, containing 10% $ZnSO_4$, illustrating the effect of $ZnSO_4$ on PLGA film water absorption.

$Mg(OAc)_2$ containing films showed an initial water uptake that was larger than the blank films (FIG. 5), but not as large as those with the insoluble magnesium salts. No additional water uptake was observed until after 21 days, when a second phase of water uptake took place. The onset of secondary water uptake was delayed by a few days relative to the blank film. Water uptake behavior by $Zn(OAc)_2$, $MgSO_4$ and $ZnSO_4$ films was similar to that of the $Mg(OAc)_2$ film samples (FIGS. 6–8).

EXAMPLE III

Effect of Salts on Polymer Degradation

The effects of encapsulated salts on polymer degradation rates were assessed by molecular weight determinations by gel permeation chromatography (GPC). The films prepared in Example I were hydrated as described in Example II. The film samples were redissolved in chloroform (5–10 mg/mL) and were filtered through a 0.22 micron filter. GPC was conducted using a MIXED column (300×10 mm, Polymer Labs) with chloroform as eluent and refractive index for detection. Molecular weights were calculated using polystyrene as standards (580 to 950,000 Daltons) and the universal calibration method.

Figure 9:
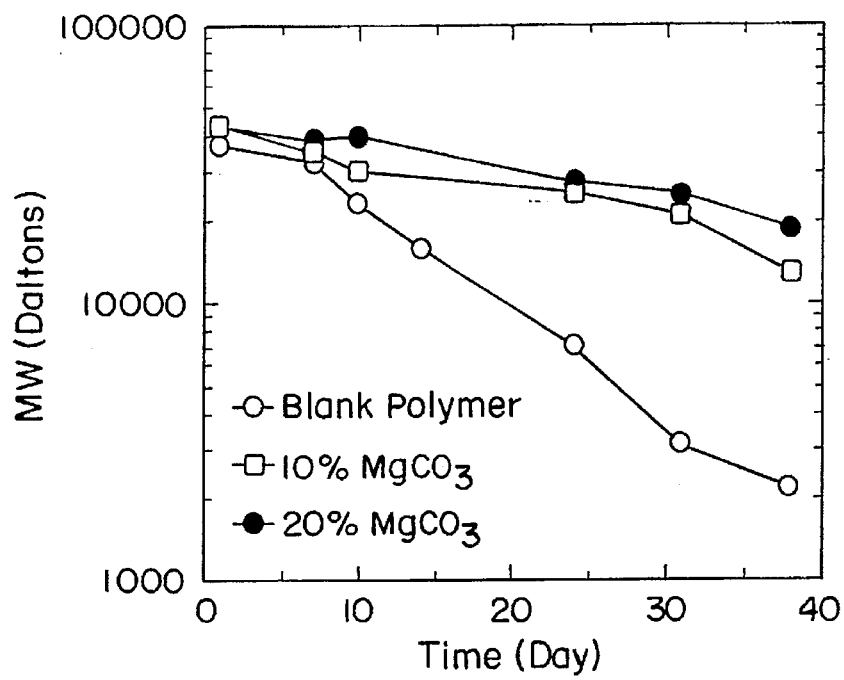
FIG. 9 is a plot of molecular weight as a function of hydration time in 10 mM HEPES for the following polymer films: a) blank PLGA, b) PLGA containing 10% $MgCO_3$, and c) PLGA containing 20% $MgCO_3$, illustrating the effects of $MgCO_3$ at different concentrations on the changes in molecular weight of PLGA films due to hydration.

The molecular weight of the control films decreased from 42000 to 3000 Daltons after 30 days as shown in FIG. 9.

Figure 10:
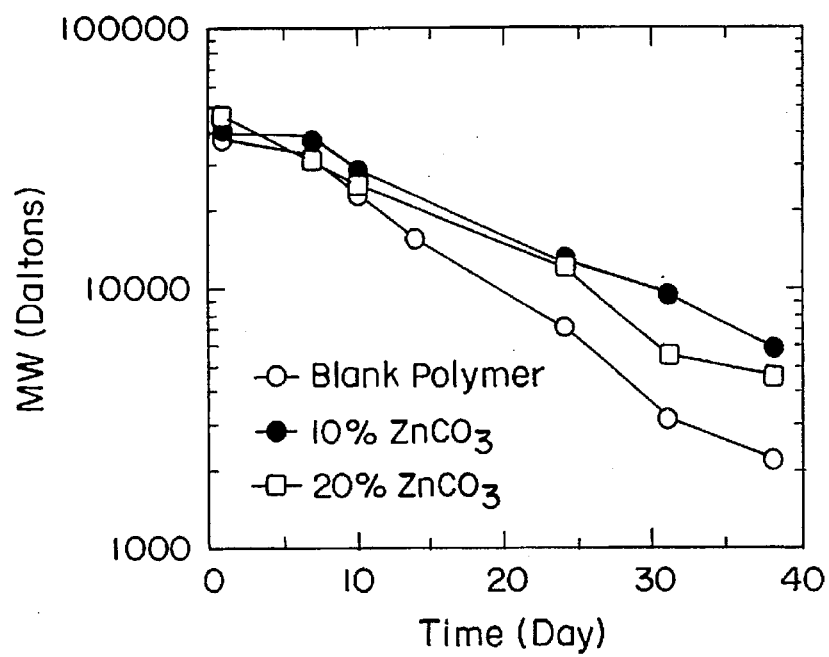
FIG. 10 is a plot of molecular weight as a function of hydration time in 10 mM HEPES for the following polymer films: a) blank PLGA, b) PLGA containing 10% $ZnCO_3$, and c) PLGA containing 20% $ZnCO_3$, illustrating the effects of $ZnCO_3$ at different concentrations on the changes in molecular weight of PLGA films due to hydration.
Figure 11:
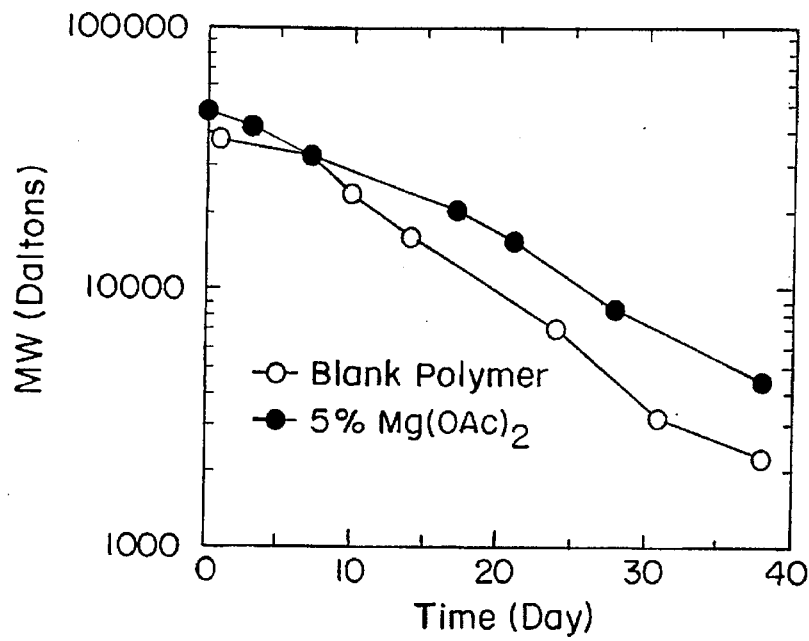
FIG. 11 is a plot of molecular weight (Mw) as a function of hydration time in 10 mM HEPES for the following polymer films: a) blank PLGA and b) PLGA containing 10% $Mg(OAc)_2$, illustrating the effects of $Mg(OAc)_2$ on the molecular weight of PLGA.

In contrast, the rate of decrease in molecular weight of the films containing $MgCO_3$ were smaller than for the control film (see FIG. 9). The molecular weight decrease in films with $ZnCO_3$ was slower than in control films (FIG. 10), but more rapid than in films containing $MgCO_3$. Similar degradation kinetics were observed with $Mg(OAc)_2$ containing films (FIG. 11).

EXAMPLE IV

Effect of Salts on Glass Transition Temperature

The glass transition temperature (Tg) of the films was determined using a differential scanning calorimeter (DSC) (DSC 7 Serial, Perkin Elmer, Norwalk, Conn.) under nitrogen and using indium as a standard. Each sample was cooled to 0° C. before heating to 60° C. at 10° C./min. Tg measurements were performed on the film samples after lyophilization as described in Example II.

Figure 12:
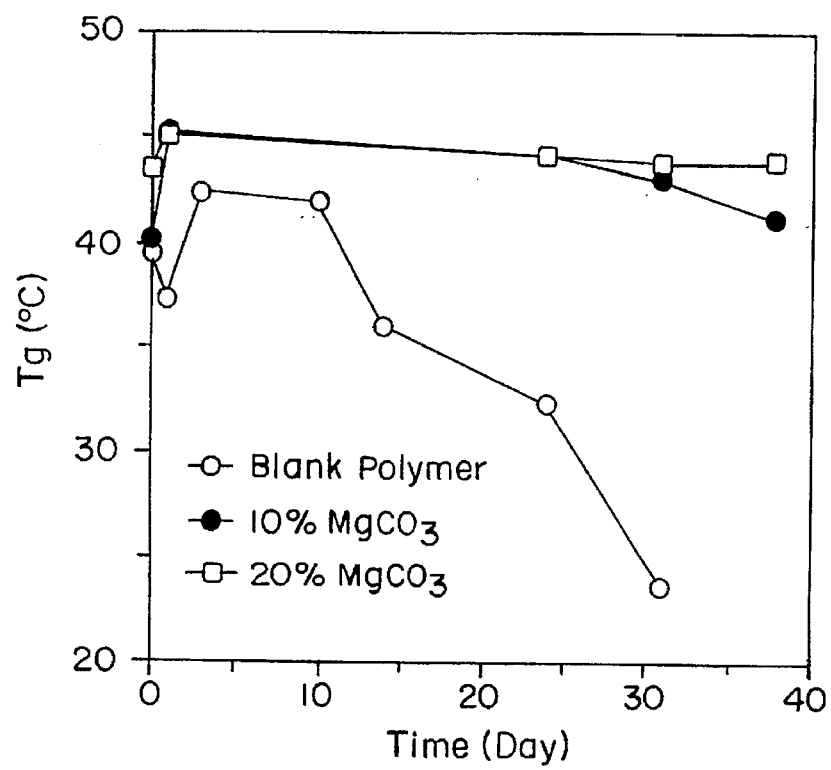
FIG. 12 is a plot of glass transition temperature (Tg) as a function of hydration time in 10 mM HEPES for the following polymer films: a) blank PLGA, b) PLGA containing 10% $MgCO_3$, and c) PLGA containing 20% $MgCO_3$, illustrating the effects of $MgCO_3$ at different concentrations on the changes in the glass transition temperature of PLGA due to hydration.

The time course of Tg decrease for control films is plotted in FIG. 12. The drop in Tg observed between 10 and 15 days corresponds to the point at which the polymer MW decreases to less than 20,000 Daltons.

Figure 13:
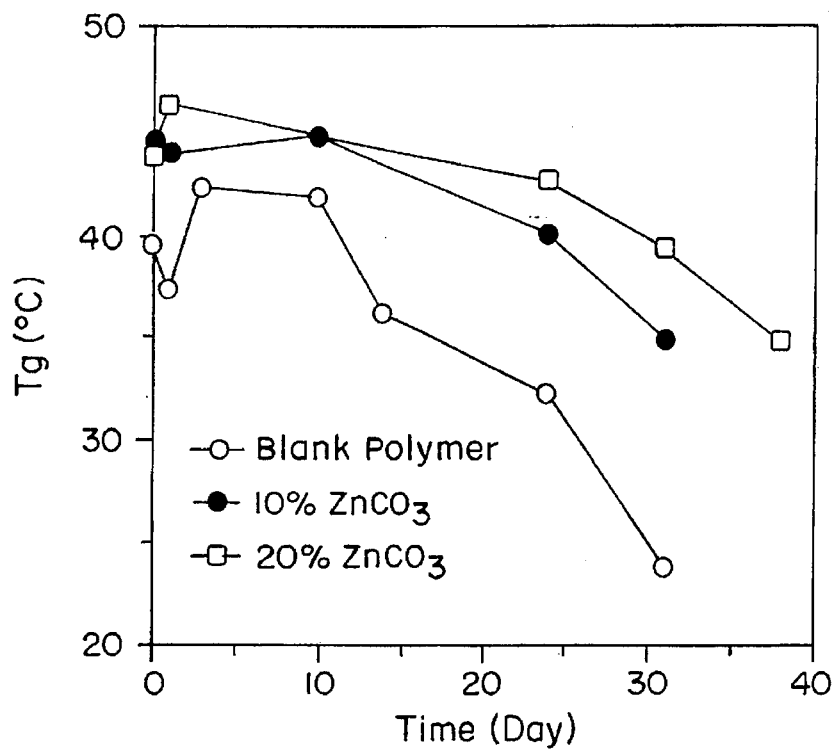
FIG. 13 is a plot of glass transition temperature (Tg) as a function of hydration time in 10 mM HEPES for the following polymer films: a) blank PLGA, b) PLGA containing 10% $ZnCO_3$, and c) PLGA containing 20% ZnCOB, illustrating the effects of $ZnCO_3$ at different concentrations on the changes in the glass transition temperature of PLGA due to hydration.
Figure 14:
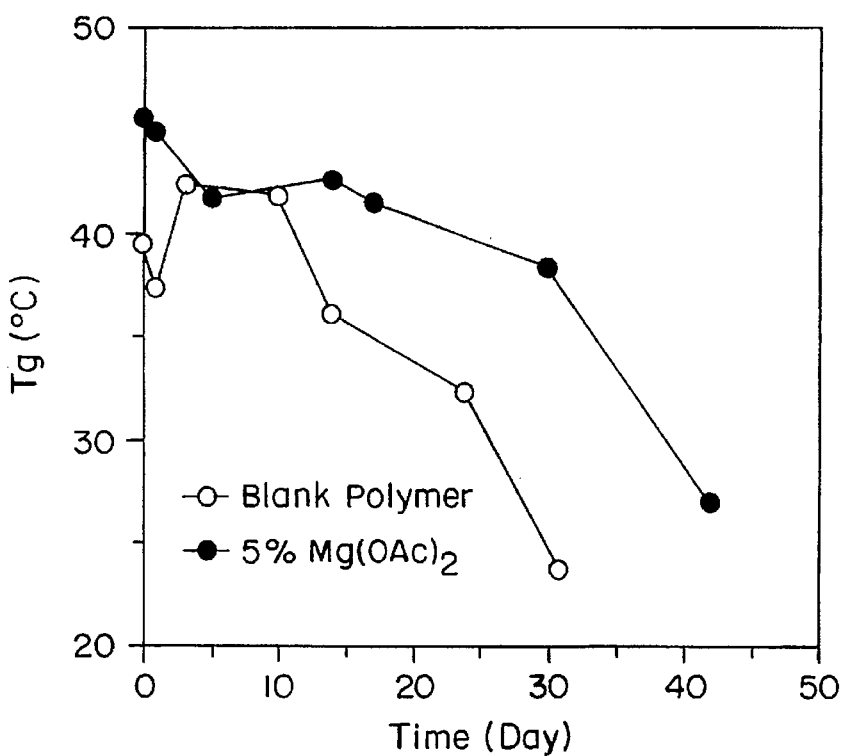
FIG. 14 is a plot of glass transition temperature (Tg) as a function of hydration time in 10 mM HEPES for the following polymer films: a) blank PLGA and b) PLGA containing 5% $Mg(OAc)_2$, illustrating the effects of $Mg(OAc)_2$ on the changes in glass transition temperature of PLGA due to hydration.

In contrast, the rates of Tg decrease in polymer films that contained Mg and Zn salts (FIGS. 12–14) were either negligible (in the case of $MgCO_3$, FIG. 12), or significantly slower ($ZnCO_3$ and $Mg(OAc)_2$; FIGS. 13 and 14, respectively) than those of control films. In $MgCO_3$ and $ZnCO_3$ containing films, a trend toward a slower Tg decrease with increasing salt content was observed.

EXAMPLE V

Effect of Salts on Film Porosity

SEM was used to observe qualitative changes in film porosity and to monitor morphology changes of the film surfaces and cross sections over time. Samples were lyophilized as described in Example II. The dried samples were sputter-coated with gold 200–300 A and the samples observed using JEOL-6400 SEM.

All films displayed a dense structure with a few pores scattered throughout the device prior to hydration. However, the rate of water uptake was different depending on the incorporated salt. Thus the increase in water uptake was not dominated by initial porosity of the sample but was a function of the type of salt dispersed in the polymer film.

SEM evaluation of the control films without salts demonstrated a dense and smooth structure up to 14 days of hydration. Between 14 and 22 days, large pores became visible on the film surface and throughout the sample cross section. The appearance of these pores coincides with the secondary water uptake phase associated with polymer degradation and erosion of the polymer (see Examples II–IV).

Films loaded with water insoluble salts exhibited increasing porosity after hydration times as short as 24 hours. SEM analysis of 24 hour hydration samples of films containing 2% $MgCO_3$ showed the formation of a porous network within the film sample, concentrated at the film surface. After 7 days, the film had become uniformly porous across the cross section. Pores ranged in diameter from approximately 1–20 μm. No further increase in porosity was observed between 7 days and 22 days. Similar behavior was observed with films that contained higher $MgCO_3$ percentages.

Films that contained 10% $ZnCO_3$ were also observed to become highly porous within 3 days of hydration. Three day hydration samples showed the presence of a porous network extending throughout the entire film cross section. The morphology of hydrated $ZnCO_3$ containing films was similar to hydrated films with $MgCO_3$.

Films that contained water soluble magnesium salts also exhibited the formation of internal and surface pores and voids well before pore formation occurred in control films. Pores ranging in diameter from approximately 1–50 μm were visible in samples that had been hydrated for five days.

There was some difference between the morphology of the films loaded with soluble and insoluble salts that were hydrated for 5 to 7 days. The films loaded with $Mg(OAc)_2$ seemed to display a lower porosity and a tendency toward large voids (approximately 50 microns) compared to films that contained insoluble salts. $MgCO_3$ and $ZnCO_3$ films showed a higher porosity; a majority of the pore volume was composed of pores of less than ten microns in diameter.

EXAMPLE VI

Effect of Salts on Polymer Weight Loss

The effects of insoluble salts on polymer degradation in hydrated film samples were also assessed by monitoring the time course of polymer weight loss during incubation. The films prepared in Example I were hydrated as described in Example II. Samples were recovered at the indicated time intervals and freeze-dried as described in Example II. The weights of the dried film samples were measured after lyophilization. Percent weight loss at different times was computed according to the equation:

$$\% \text{ Weight Loss } (t) = 100 \times (W_{initial} - W_t)/W_{initial}$$

where $W_{initial}$ is the initial weight of the polymer film and $W_t$ is the weight of the sample at time point t.

Figure 15:
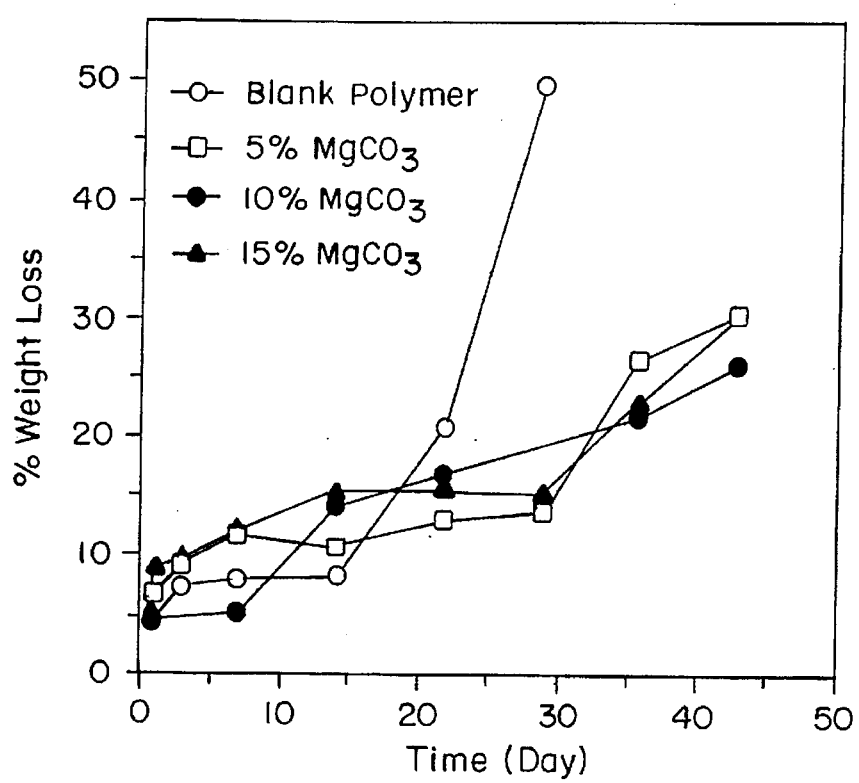
FIG. 15 is a plot of percent weight loss as a function of hydration time in 10 mM HEPES for the following polymer films: a) blank PLGA, b) PLGA containing 5% $MgCO_3$, c) PLGA containing 10% MgCOB, and d) PLGA containing 15% $MgCO_3$, illustrating the effects of $MgCO_3$ at different concentrations on the degradation of PLGA due to hydration.

The time course of weight loss in the control film is shown in FIG. 15. There is little weight loss until 14 days, after which rapid weight loss takes place. This phase of weight loss is associated with degradation and erosion of the polymer, as evidenced by increased water uptake, decreased molecular weight and Tg and the appearance of pores and voids in SEMs of film samples (see Examples II, III, V and VI). Also shown in FIG. 15 are weight loss profiles for polymer films that contain 5, 10 and 15% $MgCO_3$. Instead, weight loss in these films was more gradual and of a lesser magnitude.

A portion of the weight loss occurring in $MgCO_3$-containing films was due to dissolution of the encapsulated salt particles. To assess how closely total weight loss measurements approximate polymer weight loss in salt-containing film samples, the polymer weight loss was estimated according to the following two extreme scenarios: (1) all of the encapsulated salt dissolved between the initial hydration and the first time point, and (2) no salt dissolved throughout the entire study. Regardless of which salt dissolution scenario was selected, polymer weight loss in control films exceeded that of $MgCO_3$-containing films, indicating that incorporation of the insoluble salt prevented or delayed erosion of the polymeric matrix.

EXAMPLE VII

Effect of Salts on the Release of RNase-A or ACTH from PLGA Microspheres

RNase-A was microencapsulated into 5000 Dalton PLGA, (I.V. 0.15 dL/g Birmingham Polymers, Birmingham, Ala.) with either $ZnCO_3$ or $Mg(OH)_2$. Adrenocorticotropin hormone (ACTH) was microencapsulated into the same type PLGA with $MgCO_3$. The method described in U.S. Pat. No. 5,019,400, issued to Gombotz et al. was used to encapsulate the RNase-A and ACTH proteins. Each protein (10% w/w) and the salts (0%, 5%, 10% or 15% w/w) were added separately as particulates to a solution of PLGA in methylene chloride which was sonicated at 4° C. for 30 seconds. The suspension was then sprayed into liquid nitrogen which was overlaying frozen ethanol. The methylene chloride was extracted into the ethanol at −80° C. The microspheres were filtered and lyophilized to produce a dry powder.

The effect of the salts upon the in vitro release kinetics of RNase-A and ACTH was assessed. Release studies were conducted by suspending 20 mg of microspheres in 1 mL of 10 mM HEPES buffer at 37° C. Assays were done in 2 mL polypropylene Eppendorf tubes. Release studies of ACTH were conducted in the same manner with the exception of using PBS in lieu of HEPES buffer. At the specified time points, the buffer was removed in full and replaced with fresh buffer. The concentration of RNase-A in buffer was measured using the BCA Protein Assay (Pierce, Rockford, Ill.) and the concentration of ACTH was measured using the Biorad Protein assay (Biorad, Richmond, Calif.).

Figure 16:
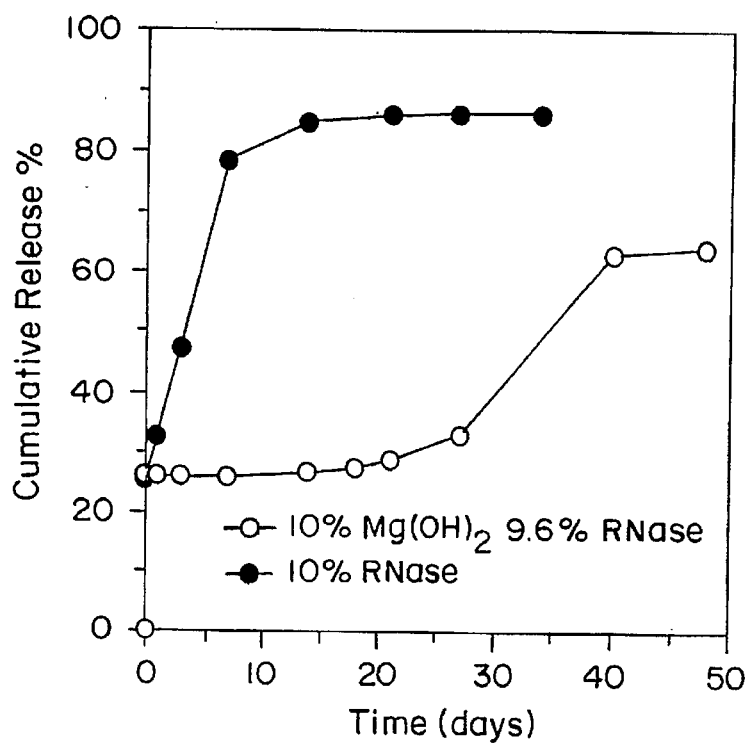
FIG. 16 is a plot of the cumulative percent release of RNase-A in 10 mM HEPES from PLGA microspheres containing 10% RNase-A and either 0% $Mg(OH)_2$ or 10% $Mg(OH)_2$, illustrating the effects $Mg(OH)_2$ on RNase-A release kinetics from PLGA microspheres due to hydration.
Figure 17:
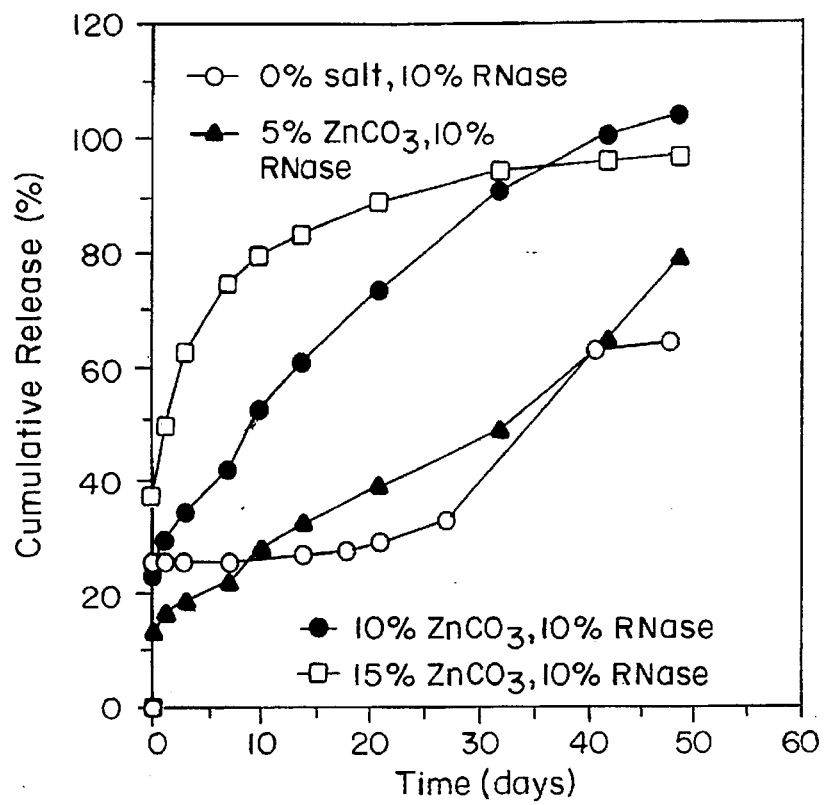
FIG. 17 is a plot of the cumulative percent release of RNase-A in 10 mM HEPES from PLGA microspheres containing 10% RNase-A and either 0% $ZnCO_3$, 5% $ZnCO_3$, 10% $ZnCO_3$, or 15% $ZnCO_3$, illustrating the effects $ZnCO_3$ on RNase-A release kinetics from PLGA microspheres due to hydration.

The effects of $ZnCO_3$ or $Mg(OH)_2$ on the release kinetics of RNase-A are shown in FIGS. 16 and 17. RNase-A encapsulated into PLGA alone exhibited release of the protein over the first 24 hours after which no further release was observed until day twenty one. $Mg(OH)_2$ resulted in continuous release of the protein over days. $ZnCO_3$ resulted in continuous release of the protein over thirty five days.

Figure 18:
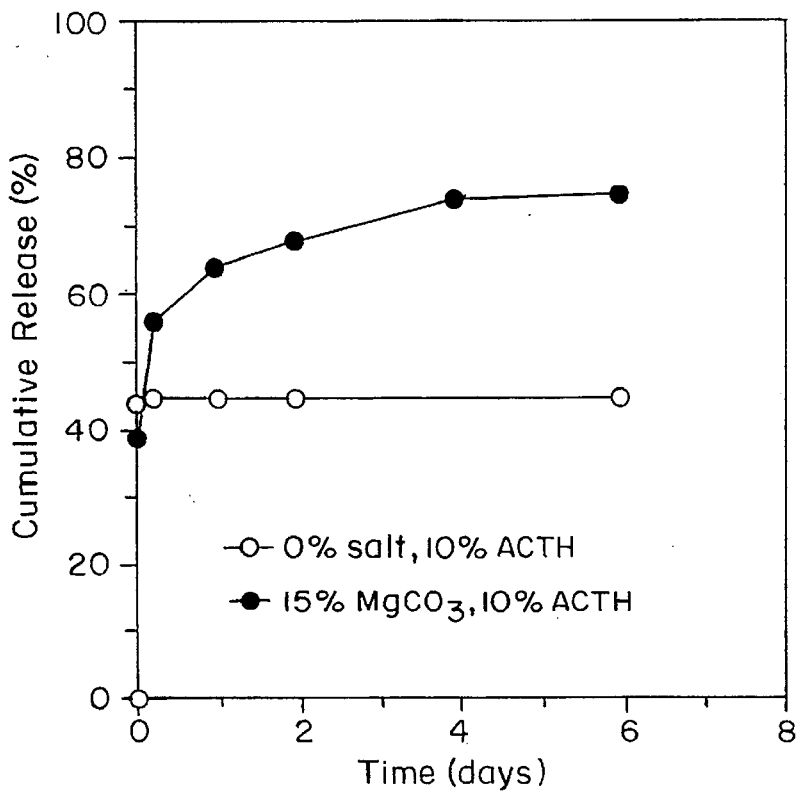
FIG. 18 is a plot of the cumulative percent release of adrenocorticotropin hormone (ACTH) in 50 mM PBS from PLGA microspheres containing 10% ACTE and either 0% $MgCO_2$ or 15% $MgCO_3$, illustrating the effects $MgCO_3$ on ACTH release kinetics from PLGA microspheres due to hydration.

The effect of $MgCO_3$ on the release kinetics of ACTH is shown in FIG. 18. ACTH encapsulated into PLGA alone exhibited approximately 40% release of the protein over the first 24 hours after which no further release was observed. $MgCO_3$ resulted in continuous release of the protein over the same period.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

The invention claimed is:

1. A pharmaceutical composition for the modulated release of a biologically active pharmaceutical agent, comprising:

a) a biocompatible and biodegradable polymeric matrix;

b) an effective amount of a biologically active pharmaceutical agent, the biologically active pharmaceutical agent being dispersed within the polymeric matrix; and c) a metal cation component for modulating release of the biologically active agent from the polymeric matrix, wherein the metal cation component comprises a cation selected from the group consisting of Zn(II), Mg(II) and a combination of at least two different multivalent metal cations, and wherein the metal cation component is separately dispersed within the polymeric matrix.

2. A modulated release composition of claim 1 wherein said metal cation component is selected from the group consisting of magnesium hydroxide, magnesium carbonate, zinc carbonate, magnesium acetate, zinc acetate, magnesium chloride, zinc chloride, magnesium sulfate, zinc sulfate, magnesium citrate and zinc citrate.

3. A composition for the modulated release of a biologically active pharmaceutical agent, comprising:
   a) a biocompatible and biodegradable polymeric matrix;
   b) an effective amount of a biologically active pharmaceutical agent, the biologically active pharmaceutical agent being dispersed within the polymeric matrix; and
   c) a metal cation component for modulating the release of the biologically active agent from the polymeric matrix, wherein said metal cation component is selected from the group consisting of magnesium hydroxide, magnesium carbonate, calcium carbonate, zinc carbonate, magnesium acetate, zinc acetate, magnesium chloride, zinc chloride, magnesium sulfate, zinc sulfate, magnesium citrate and zinc citrate, and wherein the metal cation component is separately dispersed within the polymeric matrix.

4. A method for significantly stabilizing the glass transition temperature for a polymeric matrix during hydration, comprising the steps of:
   a) forming a solution of a polymer;
   b) dispersing a metal cation component into said polymer solution; and
   c) solidifying said polymer from said polymer solution to form a polymeric matrix, containing the metal cation component dispersed therein, thereby stabilizing the glass transition temperature for a polymeric matrix during hydration.

5. A method for enhancing the initial hydration capacity of a polymeric matrix without significant polymer degradation, comprising the steps of:
   a) forming a solution of a biodegradable polymer in a solvent;
   b) dispersing a metal cation component within said polymer solution; and
   c) solidifying said polymer from said polymer solution to form a polymeric matrix, containing the metal cation component dispersed therein, thereby enhancing the initial hydration capacity of a polymeric matrix without significant polymer degradation.

6. A method for increasing the porosity of a polymeric matrix, comprising the steps of:
   a) forming a solution of a polymer and a solvent;
   b) dispersing a metal cation component within said polymer solution;
   c) solidifying said polymer from said polymer solution, to form a polymeric matrix containing the metal cation component dispersed therein; and
   d) hydrating said polymeric matrix to thereby form at least one gap within said polymeric matrix, thereby increasing the porosity of said polymeric matrix.

7. A modulated release composition of claim 3 wherein said biodegradable and biocompatible polymer is selected from the group consisting of poly(lactide) s, poly(glycolide) s, poly(lactide-co-glycolide)s, polyanhydrides, polyorthoesters, polyetheresters, polycaprolactone, polyesteramides, blends and copolymers thereof.

8. A composition for the modulated release of a biologically active protein, comprising:
   a) a biocompatible polymeric matrix;
   b) an effective amount of a biologically active protein, the biologically active protein being dispersed within the polymeric matrix; and
   c) a metal cation component for modulating release of the biologically active protein from the polymeric matrix, wherein the metal cation component comprises a cation selected from the group consisting of Zn(II), Mg(II) and a combination of at least two different multivalent metal cations, and wherein the metal cation component is separately dispersed within the polymeric matrix.

9. A modulated release composition of claim 8 wherein said polymer is biodegradable.

10. A modulated release composition of claim 7 wherein said biologically active agent comprises a protein.

11. A modulated release composition of claim 10 wherein said protein is selected from the group consisting of nucleases, erythropoietin, human growth hormone, interferons, interleukins, growth factors, tumor necrosis factor, adrenocorticotropic hormone, and colony-stimulating factors.

12. A method for modulating the release of a biologically active agent from a polymeric matrix, comprising:
   a) dissolving a biocompatible polymer in a solvent to form a polymer solution;
   b) dispersing a metal cation component in said solvent, wherein the metal cation component comprises a metal cation selected from the group consisting of Zn(II), Mg(II) and a combination of at least two different multivalent metal cations;
   c) separately dispersing a biologically active agent in said polymer solution; and
   d) solidifying said polymer from said polymer solution to form a polymeric matrix, whereby the metal cation component modulates the release of the biologically active agent from the polymeric matrix.

13. A composition for the modulated release of a biologically active agent, comprising:
   a) a biocompatible polymeric matrix of a polymer selected from the group consisting of poly(lactide)s, poly(glycolide)s, poly(lactide-co-glycolide)s and blends thereof;
   b) an effective amount of a biologically active protein, said biologically active protein being dispersed within the polymeric matrix; and
   c) a metal cation component for modulating release of the biologically active agent from the polymeric matrix, wherein said metal cation component is selected from the group consisting of magnesium hydroxide, magnesium carbonate, calcium carbonate, zinc carbonate, magnesium acetate, zinc acetate, magnesium sulfate, zinc sulfate, magnesium chloride, zinc chloride, zinc citrate and magnesium citrate, and wherein the metal cation component is separately dispersed within the polymeric matrix.

14. A modulated release composition of claim 13 wherein said biologically active protein is selected from the group consisting of nucleases, erythropoietin, human growth hormone, interferons, interleukins, growth factors, adrenocorticotropic hormone, tumor necrosis factor and colony-stimulating factors.

15. A method of claim 12, further comprising the step of suspending particles of said metal cation component in a second solvent before dispersing the metal cation component in the polymer solution, wherein the second solvent is miscible with said first solvent, and wherein said polymer is soluble in the second solvent.

16. A method for modulating the release of a biologically active agent from a polymeric matrix, comprising:
   a) dissolving a biocompatible polymer in a solvent to form a polymer solution;
   d) dispersing a metal cation component in said solvent wherein said metal cation component is selected from the group consisting of magnesium hydroxide, magnesium carbonate, calcium carbonate, zinc carbonate, magnesium acetate, zinc acetate, magnesium sulfate, zinc sulfate, magnesium chloride, zinc chloride, zinc citrate and magnesium citrate;
   c) separately dispersing a biologically active agent in said polymer solution; and
   d) solidifying said polymer from said polymer solution to form a polymeric matrix, whereby the metal cation component modulates the release of the biologically active agent from the polymeric matrix.

17. A method of claim 16 wherein said biologically active agent comprises a protein.

18. A method of claim 17 wherein said protein is selected from the group consisting of nucleases, erythropoietin, human growth hormone, interferons, interleukins, growth factors, adrenocorticotropic hormone, tumor necrosis factor and colony-stimulating factors.

19. A method of claim 18 wherein said polymer is biodegradable.

20. A method of claim 19 wherein said biodegradable polymer is selected from the group consisting of poly (lactide)s, poly(glycolide) s, poly(lactide-co-glycolide)s, polyanhydrides, polyorthoesters, polyetheresters, polycaprolactone, polyesteramides, blends and copolymers thereof.

21. A method of claim 18 wherein said polymer is non-biodegradable.

22. A method of claim 21 wherein said non-biodegradable polymer is selected from the group consisting of polyacrylates, polymers of ethylene-vinyl acetates, and acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

23. A method of claim 15, further comprising the step of dissolving said metal cation component in a second solvent before dispersing the metal cation component in the polymer solution, wherein the second solvent is miscible with the first solvent, and wherein said polymer is soluble in the second solvent.

* * * * *

UNITED STATES PATENT AND TRADEMARK OFFICE
CERTIFICATE OF CORRECTION

PATENT NO. : 5,656,297
DATED : August 12, 1997
INVENTOR(S) : Howard Bernstein, Yan Zhang, M. Amin Khan, Mark A. Tracy It is certified that error appears in the above-identified patent and that said Letters Patent is hereby corrected as shown below:

On the title page, between item [73 and item [21], delete
"[*] Notice: The portion of the term of this patent subsequent to
Jul. 25, 2014, has been disclaimed."

Signed and Sealed this

Sixth Day of January, 1998

Attest:

BRUCE LEHMAN

Attesting Officer     Commissioner of Patents and Trademarks